United States Patent [19]
Helmling et al.

[11] Patent Number: 5,539,109
[45] Date of Patent: Jul. 23, 1996

[54] FIBER-REACTIVE TRIPHENODIOXAZINE DYES

[75] Inventors: Walter Helmling, Niedemhausen; Uwe Reiher, Hofheim, both of Germany

[73] Assignee: Hoechst Celanese Corporation, Somerville, N.J.

[21] Appl. No.: 481,420

[22] PCT Filed: Mar. 24, 1994

[86] PCT No.: PCT/US94/03233

§ 371 Date: Jul. 11, 1995

§ 102(e) Date: Jul. 11, 1995

[87] PCT Pub. No.: WO94/21646

PCT Pub. Date: Sep. 29, 1994

Related U.S. Application Data

[63] Continuation-in-part of Ser. No. 36,611, Mar. 24, 1993, abandoned.

[51] Int. Cl.⁶ .................................................. C07D 498/04
[52] U.S. Cl. .................................................. 544/76
[58] Field of Search ................................... 544/76

[56] References Cited

U.S. PATENT DOCUMENTS 4,780,107  10/1988  Sawamoto et al. ........................ 8/657
5,227,475   7/1993  Buch et al. ............................ 534/629

FOREIGN PATENT DOCUMENTS

90/13604  11/1990  WIPO ........................... C09B 62/503

Primary Examiner—Philip I. Datlow
Attorney, Agent, or Firm—Hugh C. Crall

[57] ABSTRACT

The invention is that of a new triphenodioxazine dye of the formula:

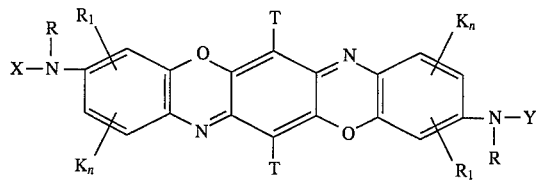

wherein:

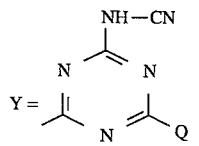

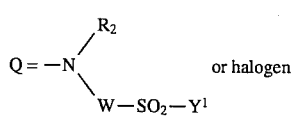

K is independently selected from $SO_3H$ and COOH;

W= a substituted or unsubstituted arylene, alkylene or arylene-alkylene group;

$Y^1$ = Vinyl, β-Sulfatoethyl, β-Thiosulfatoethyl, β-Halogenethyl-group, β-Phosphatoethyl, and

X=H.

R, $R_1$ and $R_2$ are independently selected from hydrogen and substituted or unsubstituted alkyl.

T is independently selected from hydrogen, Cl, Br, $C_1$ to $C_6$ alkyl, $C_1$ to $C_6$ alkoxy, phenyl or phenoxy; and n is selected from 0, 1 or 2.

4 Claims, No Drawings

FIBER-REACTIVE TRIPHENODIOXAZINE DYES

CROSS REFERENCES TO RELATED APPLICATIONS

This is a 35USC371 national stage application of PCT/US94/03233, filed Mar. 24, 1994, and is a continuation-in-part of U.S. patent application Ser. No. 08/036,611 filed Mar. 24, 1993 now; abandoned.

BACKGROUND OF THE INVENTION

1. Technical Field

This invention is directed to new fiber reactive triphenodioxazine dye.

2. Background

Anthraquinone based fiber reactive dyes have been the predominate dye used in the coloring of cotton fabdcs in bright blue colors. This dominance of the anthraquinone dyes has been threatened over the past decade or so by the increasing use of dyes based upon the triphenodioxazine chromophore.

Examples of the recent patent activity in this triphenodioxazine based dyes are: U.S. Pat. No. 4,604,459; U.S. Pat. No. 3,996,221; U.S. Pat. No. 4,092,478; U.S. Pat. No. 4,400,504; U.S. Pat. No. 4,472,575; U.S. Pat. No. 4,774,333; U.S. Pat. No. 4,629,788; and EPO 385,120 (Sep. 9, 1990).

The present invention provides new dioxazine based fiber reactive dyes with good fastness properties (light, chlorine and wash fastness), high substantivity for cellulosic fibers, high tinctorial strength and a bright reddish blue color. In addition, the dyes of the invention are easily synthesized from readily available intermediates at low costs.

SUMMARY OF THE INVENTION

The invention is that of a new triphenodioxazine dye of the formula:

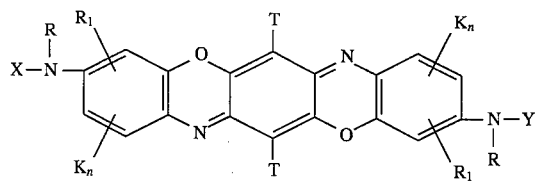

wherein:

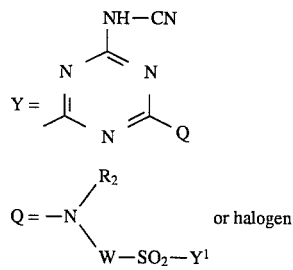

W=a substituted or unsubstituted arylene, alkylene or arylene-alkylene group where the alkylene moiety may be interrupted by a hetero atom selected from O, S and N;

$Y^1$=Vinyl, β-Sulfatoethyl, β-Thiosulfatoethyl, β-Halogenethyl, β-Phosphatoethyl, and

X=H.

K is independently selected from $SO_3H$ and COOH.

R, $R_1$ and $R_2$ are independently selected from hydrogen and substituted or unsubstituted alkyl of 1 to 6 carbons; preferably hydrogen and a substituted or unsubstituted $C_1$ to $C_4$ alkyl.

$R_2$ may also be selected from the group $W—SO_2—Y^1$.

T is independently selected from hydrogen, Cl, Br, $C_1$ to $C_6$ alkyl, $C_1$ to $C_6$ alkoxy, phenyl or phenoxy; and n is selected from 0, 1 or 2.

The dyes of the above formula provide dyeing on cotton substrates having a bright reddish blue color having good fastness or properties of high tinctodal strength. The dyes of the invention may also be used in the dyeing of other textiles containing amido and/or hydroxyl groups; exemplary materials include regenerated cellulose, synthetic polyamides, wool, silk and polyurethane fibers. The dyes of the invention may be applied by the standard methods for printing and dyeing textiles with fiber reactive dyes.

DESCRIPTION OF THE PREFERRED EMBODIMENTS

The invention relates to new triphendioxazine reactive dyestuffs of the formula:

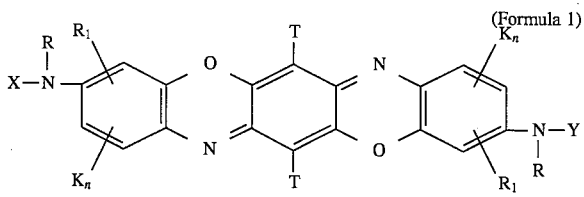

wherein:

R and $R_1$ are independently selected from H or a substituted or unsubstituted alkyl, preferably hydrogen or a substituted or unsubstituted $C_1$-$C_6$- alkyl, and most preferably hydrogen or a substituted or unsubstituted $C_1$-$C_4$ alkyl;

T is independently selected from H, Cl, Br, a substituted or unsubstituted $C_1$-$C_4$-alkyl, $C_1$-$C_4$-alkoxy, phenyl, or phenoxy;

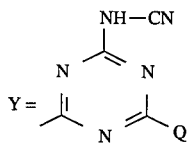

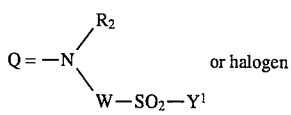

$R_2$ iS selected from hydrogen or a substituted or unsubstituted $C_1$ to $C_6$ alkyl or the group $W—SO_2—Y^1$; preferably hydrogen or a substituted or unsubstituted $C_1$ to $C_4$ alkyl.

W is a substituted or unsubstituted arylene, or alkylene, or arylene-alkylene group wherein the alkylene group may be interrupted by a hetero atom selected from O, S and N, preferably a substituted or unsubstituted phenylene or naphthalene group or a substituted or unsubstituted $C_1$ to $C_6$ alkylene group, wherein said alkylene moiety may be interrupted by a hetero atom selected from O, N and S; $Y^1$= Vinyl, β-Sulfatoethyl, β-Thiosulfatoethyl, β-Halogenethyl, β-Phosphato, and X=H. K is independently selected from $SO_3H$ and COOH. n=0, 1 or 2.

The term "arylene-alkylene" group as used in this specification and the claims is intended to mean a phenylene or naphthalene group bonded to one or more alkylene groups, e.g. the following illustrations or their isomers:

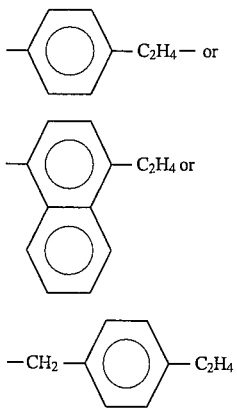

Examples of R, $R_1$ and $R_2$ are: hydrogen or $CH_3$, $C_2H_5$, n-$C_3H_7$, n-$C_4H_9$, n-$C_6H_{13}$, which may be optionally substituted by OH, $OCH_3$, $OC_2H_5$, COOH, $SO_3H$, $OSO_3H$, CN, Cl, or F.

Examples of the substituents in substituted $C_1$-$C_4$-alkyl and $C_1$-$C_4$-alkoxy, groups are OH, $OCH_3$, $OC_2H_5$, COOH, $SO_3H$, $OSO_23H$, CN, Cl, Br or F; preferably $OCH_3$, $OC_2H_5$ and $OSO_3H$.

Examples of the substituents in a substituted phenyl and phenoxy groups are Cl, Br, $CH_3$, $C_2H_5$, $OCH_3$, $SO_3H$, COOH and $OC_2H_5$.

Preferably R and $R_1$ are hydrogen; $R_2$ is preferably hydrogen, $CH_3$ or $C_2H_5$; W is preferably phenylene or naphthalene which may be substituted by methyl, methoxy, carboxy and sulfo. $Y^1$ is preferably vinyl or sulfatoethyl, X is preferably hydrogen and n is preferably 1.

Exemplary type "Q" groups are:

2-(β-Sulfatoethylsulfonyl)-phenyl-amino, 3-(β-Sulfatoethylsulfonyl)-phenyl-amino, 4-(β-Sulfatoethylsulfonyl)-phenyl-amino, 2-Carboxy- 5-(β-sulfatoethylsulfonyl)-phenyl-amino, 2-Chloro-3-(β-Sulfatoethylsuifonyl)-phenyl-amino, 2-Chloro-4-(β-sulfatoethylsulfonyl)-phenyl-amino, 2-Ethoxy-4- or 5-(β-sulfatoethylsulfonyl)-phenyl-amino,2-Ethyl-4-(β-sulfatoethylsulfonyl)-phenyl-amino, 2-Methoxy-5-(β-sulfatoethylsulfonyl)-phenyl-amino, 2,3-Dimethoxy-5-(β-sulfatoethylsulfonyl)-phenyl-amino, 2,4-Dimethoxy-5-(β-sulfatoethylsulfonyl)-phenyl-amino, 2,5-Dimethoxy-4-(β-sulfatoethylsulfonyl)-phenyl-amino, 2-Methoxy-5-methyl-4-(β-sulfatoethylsulfonyl)-phenyl-amino, 2or 3- or 4-(β-Thiosulfatoethylsulfonyl)-phenyl-amino, 2-Methoxy-5-thiosulfoethylsulfonyl)-phenyl-amino, 2-Sulfo-4-(β-phosphatoethylsulfonyl)-phenyl-amino, 2-Sulfo-4-vinylsulfonyl-phenyl-amino, 2-Hydroxy-4- or- 5-(β-sulfatoethylsulfonyl)-phenyl-amino, 2-Chloro-4-or-5-β-chloroethylsulfonyl)-phenyl-amino, 2-Hydroxy-3-sulfo-5-(β-sulfatoethylsulfonyl)-phenyl-amino, 3- or 4-(β-Acetoxyethylsu lfonyl)-phenyl-amino, 2-Methoxy-4-[β-(N-methyltauryl)ethylsulfonyl]-phenyl-amino 5-(β-Sulfatoethylsulfonyl)naphth-2-yl-amino, 6- or 7- or 8-(β-Sulfatoethylsulfonyl)-naphthy-2-yl-amino, 6-(β-Sulfatoethylsulfonyl)- 1-sulfo-naphth-2-yl-amino, 5-(β-Sulfatoethylsulfonyl)-l-sulfo-naphth-2-yl-amino, 8-(β-Sulfatoethylsulfonyl)-6-sulfo-naphth-2-yl-amino, β-[4-(β'-Sulfatoethylsulfonyl)-phen]-ethylamino, β-[-2-Sulfo-4-(β'-sulfatoethylsulfonyl)phen]ethylamino, β-(β'-Chloroethylsulfonyl)-ethylamino, β- (β'-Sulfatoethylsulfonyl)-ethylamino, β -(Vinyisulfonyl)-ethylamino, (β' -Chloroethylsulfonyl)-propylamino, γ-(β'-Sulfatoethylsulfonyl)-propylamino, γ-(β'-Bromoethylsulfonyl)-propylamino, γ -(Vinylsulfonyl)-propylamino, 1-Methyl- 1-(β-sulfatoethylsulfonyl)-1-ethylamino, δ-(β'-Sulfatoethylsulfonyl)-butylamino, 2-Methyl-2-(β-chloroethylsulfonyl)-1-propylamino, ω-(β'-Chloroethylsulfonyl)-pentylamino, β-(β'-Chloroethylsulfonyl)-n-hexyalmino, N-Methyl-N-[ β-(β'chloroethylsulfonyl)-ethyl]-amino, N-Ethyl-N-[ β-(β'-chloroethyisulfonyl)ethyl]-amino, N-n-Propyl-N-[β-(β'chloroethylsulfonyl)-ethyl]-amino, N-Carboxymethyl-N-[β-(β'-bromoethylsulfonly)-ethyl]-amino, N-Sulfatomethyl-N-[β-(β'-chloroethylsulfonyl)-ethyl]-amino, N-(β-Carboxyethyl)-N-[-γ-(β-chloroethylsulfonyl)-propyl-amino-N-(β-Sulfatoethyl)-N-[γ-(β"chloroethylsulfonyl)-propyl-amino-N-(β-(βSulfatoethyl)-N-[, δ'(β"chloroethylsulfonyl)-butyl]-amino, N-(β-Ethoxyethyl)-N-[δ'-(β"-chloroethylsulfonyl)-butyl]-amino, N-(γ-Chloropropyl)-N-[δ'(β"-chloroethylsulfonyl)-butyl]-amino, N-Phenyl-N-[β-(β'-chloroethylsulfonyl)-ethyl]-amino, N-(3-Sulfophenyl)-N-[ β-(β'-chloroethylsulfonyl)-ethyl] amino, N-( 4-Sulfophenyl)-N-[β-(β'-chloroethylsulfonyl)-ethyl]-amino,
Bis-[ β-(β'-chloroethylsulfonyl)-ethyl]-amino,
Bis-[β-(β'-bromoethylsulfonyl)-ethyl]-amino,
Bis-[γ-(β'-chloroethylsulfonyl)-propyl]-amino,
Bis-[δ-(β'-chloroethyisulfonyl)-butyl]-amino,
Bis-(β-vinylsulfonyl-ethyl)-amino, N-(β-Cyanoethyl)-N-[γ'-β"-chloroethylsulfonyl)-propyl]-amino,
β[β'-(β"-Chloroethylsulfonyl)-ethylamino]-ethylamino,
β[β'(β"- Sulfatoethylsulfonyl)-ethylamino]-ethylamino,
β-[β'(β"-Chioroethylsuifonyl)-ethoxy]-ethylamino,
β-β'-β"-Sulfatoethylsulfonyl)-ethoxy]-ethylamino,
3,4-Di-(β-sulfatoethylsulfonyl)-phenylamino,
2,5-Di(β-sulfatoethylsulfonyl)-phenylamino,
4-[γ-(β'Sulfatoethylsulfonyl)-propoxy]-phenylamino,
2,5-Bis-[(β-sulfatoethylsulfonyl)-methyl], phenylamino,
N-Methyl-N-[4-(β-sulfatoethylsulfonyl)-phenyl]-amino,
N-Methyl-N-[3-(β-sulfatoethylsulfonyl)-phenyl]-amino,
N-Ethyl-N-[4-(β-sulfatoethylsulfonyl)-phenyl]-amino,
N-Ethyl-N-[3-(β-sulfatoethylsulfonyl)-phenyl]-amino, and halogen (chloro, fluoro and bromo).

Dyestuffs which are preferred having the following general Formula 1A:

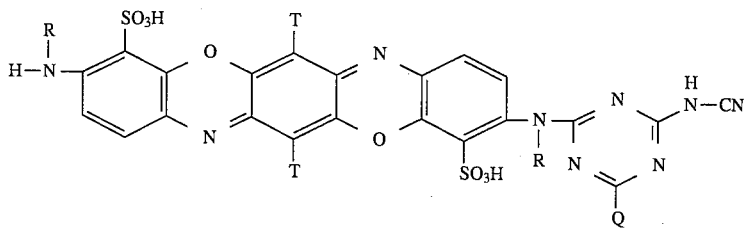

wherein $T_1$, $R$, $R_1$ and $Q$ have the above mentioned meaning.

The moiety $Q$ may be represented by the formula:

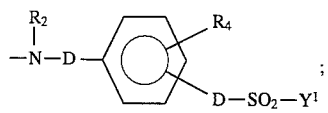

wherein $D$ is independently selected from a covalent bond or a $C_1$ to $C_6$ alkylene group which may be optionally interrupted by a hetero atom selected from O, N and S; $Y^1$ is defined above, and $R_4$ is selected from H, Cl, Br, $C_1$ to $C_4$ alkyl, $C_1$ to $C_4$ alkoxy or phenoxy and $R_2$ is as previously defined.

Preferred dyestuffs of Formula 1 are those in which

T = Cl,
n = 1,
R = H,
$R_1$ = H, and

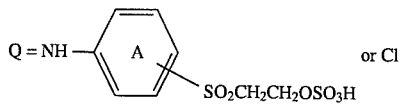

where the benzene ring A can contain further substituents. Examples of such substituents are: $CH_3$, $C_2H_5$, $OCH_3$, $OC_2H_5$, Cl, COOH, and $SO_3H$.

The invention also relates to a process for preparing the dyestuffs of the Formula 1 wherein X is hydrogen. This process is characterized in that about 1 mole of a triphenodioxazine dyestuff of the Formula 2.

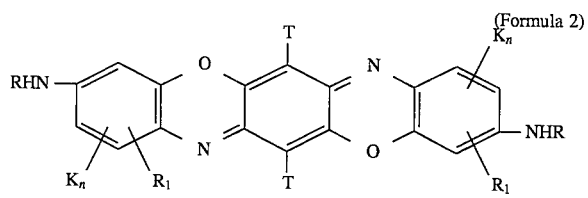
(Formula 2)

preferably in the form of the corresponding lithium salts is condensed with about 1 to 1.3 moles of 2,4,6-trichlorotriazine with elimination of 1 mole hydrochloric acid, preferably using basic lithium compounds such as lithium hydroxide or lithium carbonate as acid acceptors, to give the triphenodioxazine/dichlorotriazine condensation product, which then is reacted with about 1 mole of cyanamide of the Formula 3:

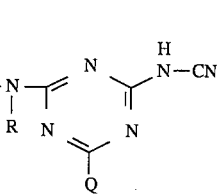
(Formula 1A)

$H_2N—CN$      (Formula 3)

with the elimination of 1 mole of hydrochloric acid. The resulting monochloromonocyanamido compound is then reacted with about 1 mole of an amine of the Formula 4:

$H—Q$      (Formula 4)

with the elimination of 1 mole hydrochloric acid to give the dyestuff of Formula 1. In both the last steps, basic alkali such as lithium hydroxide, lithium carbonate, sodium hydroxide and sodium carbonate can be used as acid acceptors.

An alternative to the above described process is the reaction of about 1 mole of 2,4,6-trichloro-triazine with 1 mole of cyanamide of the Formula 3, to the dichloromonocyanamido compound of the Formula 5.

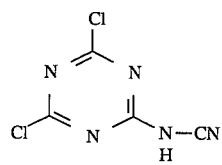
(Formula 5)

This compound is then reacted with about 1 mole of amine of the Formula 4 to give a compound of Formula 6.

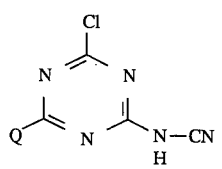
(Formula 6)

This compound is then reacted with about 1 mole of triphenodioxazine dyestuff of the Formula 2 to give the dye of Formula 1. In all steps hydrochloric acid is eliminated, which is neutralized by using a basic alkali compounds such as lithium hydroxide, lithium carbonate, sodium hydroxide and sodium carbonate.

An other alternative for preparing the dyestuffs of the Formula 1 is first reaction of 1 mole o 2,4,6-trichlorotdazine with 1 mole of cyanamide of the Formula 1 to the dichloromonocyanamido compound of Formula 5. This compound is then reacted with 1 mole of the triphenodioxazine dyestuff of the Formula 2 to give the monochloro-monocyanamido-triphendioxazine-triazine compound of Formula 7.

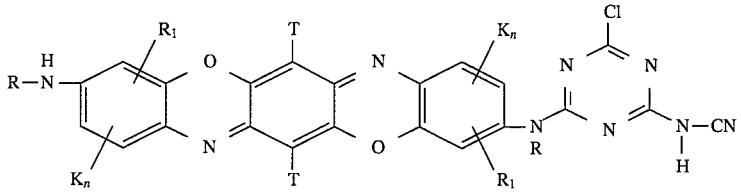

(Formula 7)

Finally the compound of Formula 7 is reacted with approximately 1 mole of an amine of the Formula 4. In all steps hydrochloric acid is eliminated, which is accepted by using basic alkali compounds such as lithium hydroxide, lithium carbonate, sodium hydroxide and sodium carbonate.

Examples of the H—Q amines are the amines of the above mentioned amine radicals Q.

The preparation of compounds of the Formula 2 is effected by methods known to those skilled in the art by condensing 1,4-benzoquinones of the formula:

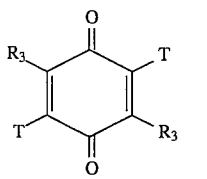

(Formula 8)

wherein

T has the above mentioned meaning and $R_3$ is independently selected from H, Cl, Br, a substituted or unsubstituted alkyl, a substituted or unsubstituted alkoxy or phenoxy, with diaminobenzenes of the formula:

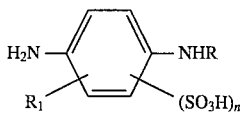

(Formula 9)

wherein R, $R_1$, and no have the above mentioned meaning, to give a compound of the formula:

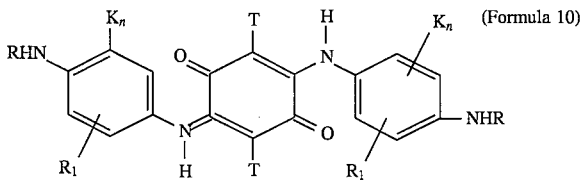

(Formula 10)

and subsequently cyclizing the diaminobenzene or dianilino compound 10 to give the basic dioxazine dyestuff of Formula 2.

The benzoquinones of Formula 8 are best condensed with the diaminobenzenes of the Formula 9 at temperatures of 0°–70° C., preferably 20°–50° C., and at pH 2–10, preferably pH 5–7, in an aqueous or aqueous-organic medium in the presence of alkaline condensing agents. It is also possible to work in a purely organic medium in the presence of acid-binding agents. The condensation products of the Formula 10 can be precipitated by salting out or by acidification.

Examples of suitable organic mediums are methanol, ethanol, and nitrobenzene. Examples of suitable acid-binding agents are sodium bicarbonate, sodium carbonate, sodium acetate, potassium acetate, sodium hydroxide, potassium hydroxide, sodium phosphates and sodium borate.

Examples of suitable diaminobenzenes of the Formula 8 are as follows: 1,4-Diaminobenzene-2-sulfonic acid, 1,4-Diaminobenzene-2-carboxy acid, 1-Amino-4-N-methylaminobenzene-3-sulfonic acid, 1-Amino-4-N-ethylaminobenzene-3-sulfonic acid, 1,4-Diamono-2-methoxybenzene-5-sulfonic acid, 1,4-Diamono-2-methylbenzene-5-sulfonic acid, 1,4-Diaminobenzene-2,5-disulfonic acid, 1,4-Diaminobenzene-2,5-dicarboxy acid, 1,4-Diamino-2-carboxybenzene-5-sulfonic acid.

The cyclization of the dianilino compounds of the Formula 10 can be effected by methods known to those skilled in the art; see e.g., U.S. Pat. No. 4,604,459 and A.H.M. Renfrew, J.Soc. Dyers Colour, 105 (1989) 262–4, GB Patent No. 1,589,915 in particular, at temperatures of 10°–80° C. in oleum having $SO_3$ contents of 1–50%, in the absence of presence of oxidizing agents such as potassium peroxodisulphate, ammonium peroxodisulphate or organic peroxides.

In general, oleum having an $SO_3$ content of 5–30% is used in an amount of about 5–15 parts by weight per part by weight of the compound of Formula 10.

Under the reactive conditions for cyclization in oleum it is possible to sulfonate aliphatic OH groups and sulfonate aromatic rings present in the dianilino compounds of the Formula 10; therefore milder conditions must be used if undesired sulfonation is encountered.

The new dyestuffs produce bright reddish blue dyeings on cellulose and natural or synthetic polyamide materials. They are distinguished by high tinctorial strength. As water-soluble reactive dyestuffs, the new dyestuffs are preferably of interest for the dyeing of hydroxyl- and amido-containing textile materials, in particular materials in natural and regenerated cellulose and synthetic polyamide and polyurethane fibers, wool and silk.

These materials may be dyed or pdnted using the methods which are commonly known and customary in industry for water-soluble reactive dyestuffs. The dyeing are then light- and wet-fast blue dyeings and prints.

The temperatures in the Examples are given in °C. The formulae of water-soluble reactive dyestuffs in the description and in the Examples are shown in the free acid form. In general, the dyestuffs are isolated and used in the form of their alkali metal salts, in particular in the form of the lithium, sodium or potassium salts. The preferred form of the fiber-reactive moiety $Y^1$ is the β-sulfatoethylsulfonyl group and the formula that follow show $Y^1$ in that form. It will be readily apparent to those skilled in the art that equivalent vinyl, phosphato thiosulfato etc. group may be used. It will also be apparent to the skilled worker that the reaction mixture may be a mixture of fiber reactive moieties and depending on the reaction conditions e.g. up to 30% of the vinyl moiety and up to about 5% of the non-reactive hydroxy moiety may be formed.

EXAMPLE 1

21.8 parts of 2,9-diamino-6,13-dichlorotriphenodioxazine-1,8-disulfonic acid is suspended in 1000 parts of water and brought to pH 7.0 by using an aqueous solution of 5% LiOH. The reaction mixture is stirred for one hour until complete solution. The pH is adjusted with hydrochloric acid to 4.5 and 7.8 parts of 2,4,6-tdchlorotriazine is added. The reaction mixture is stirred for 3 hours at room temperature and the pH maintained at 4.5 using an aqueous solution of 5% LiOH. To the resulting pdmary condensation product 2.5 parts of cyanamide in form of a 50% aqueous solution is added and the pH adjusted to 9.0 using LiOH. The reaction mixture is heated up to 45°-40° C. for 3 hours by maintaining the pH. After adjusting the pH to 4.0 of the resulting secondary condensation product, 14.0 pans of 1-amino-3-[βsulfatoethylsulfonyl]-benzene is added. After stirring for 6 hours at 80° C. at pH 5.5 the reaction is completed. High performance liquid chromatography can be used in all steps to indicate the end of each condensation.

The reaction mixture is stirred for 3 hours at room temperature and the pH maintained at 4.5 using an aqueous solution of 5% LiOH. The resulting primary condensation product 2.5 parts of cyanamide in form of a 50% aqueous solution is added and the pH adjusted to 9.0 using LiOH. The reamion mixture is heated up to 45°-40° C. for 3 hours by maintaining the pH. After adjusting the pH to 4.0 of the resulting secondary condensation product, 14.0 parts of 1-amino-3-[β-sulfatoethyl-sulfonyl]-5-methoxy-benzene is added. After stirring for 6 hours at 80° C. at pH 5.5 the reaction is completed. High performance liquid chromatography can be used in all steps to indicate the end of each condensation. The resulting dyestuff solution is clarified and spray dried. It results in a blue dyestuff powder, which, if applied to cotton in one of the methods customary for reactive dyestuffs, product brilliant strongly reddish bluish shades. The dyestuff in form of the free acid has the following formula:

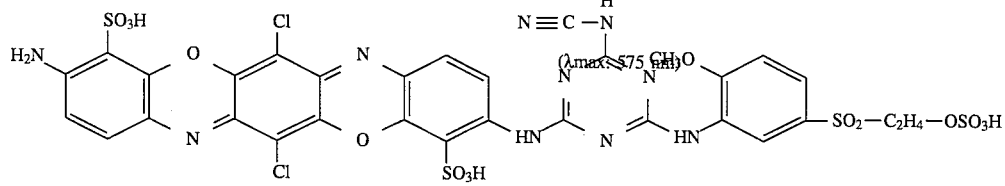

The resulting dyestuff solution is clarified and spray dried. It results in a blue dyestuff powder, which, if applied to cotton in one of the methods customary for reactive dyestuffs, produces brilliant strongly reddish bluish shades.

The dyestuff in form of the free acid has the following formula:

Additional dyestuffs of the following general Formula A. These compound shades dye cotton in bright, strong, reddish blue shades are obtained by using the procedure of the above examples.

(λmax: 574 nm)

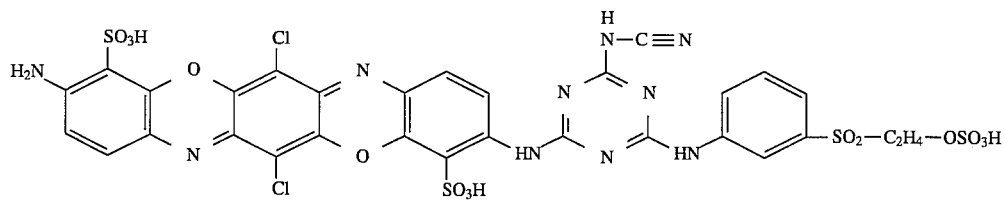

EXAMPLE 2

21.8 pans of 2,9-diamino-6,13-dichlorotriphenodioxazine-1,8-disulfonic acid is suspended in 1000 pans of water and brought to pH 7.0 by using an aqueous solution of 5% LiOH. The reamion mixture is stirred for one hour until complete solution. The pH is adjusted with hydrochloric acid to 4.5 and 7.8 pans of 2,4,6-trichlorotriazine is added.

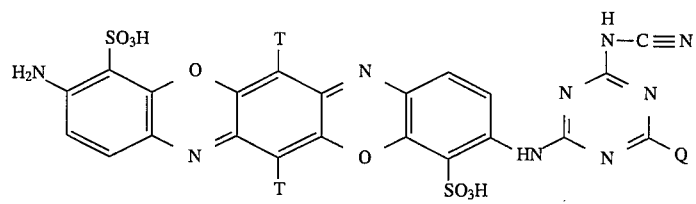

(Formula A)

Examples 3–31 illustrate compounds of the general Formula A wherein the substituents T and Q are as follows:

EXAMPLES 3–31

| Ex. | T | Q |
|---|---|---|
| 3 | Cl | —NH—[2,5-di(OCH₃)-phenyl]—SO₂—CH₂—CH₂—OSO₃H |
| 4 | Cl | —NH—[4-OCH₃-phenyl]—SO₂—CH₂—HC₂—OSO₃H (3-position) |
| 5 | Cl | —NH—[2-OCH₃, 5-CH₃-phenyl]—SO₂—CH₂—CH₂—OSO₃H |
| 6 | Cl | —N(CH₃)—[3-(SO₂—CH₂—CH₂—OSO₃H)-phenyl] |
| 7 | Cl | —N(CH₃)—[4-(SO₂—CH₂—CH₂—OSO₃H)-phenyl] |
| 8 | Cl | —NH—[1-SO₃H, 6-(SO₂—CH₂—CH₂—OSO₃H)-naphth-2-yl] |
| 9 | Cl | —NH—[1-(SO₂—CH₂—CH₂—OSO₃H), 3-SO₃H-naphth-6-yl] |
| 10 | Cl | —NH—[4-CH₃, 3-(SO₂—CH₂—CH₂—OSO₃H)-phenyl] |
| 11 | Cl | —NH—CH₂—CH₂—[4-(SO₂—CH₂—CH₂—OSO₃H)-phenyl] |
| 12 | Cl | —NH—[2-SO₃H, 5-(SO₂—CH₂—CH₂—OSO₃H)-phenyl] |

-continued
| Ex. | Q | T |
|---|---|---|
| 13 | Cl | 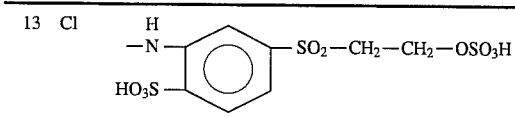 |
| 14 | Br | 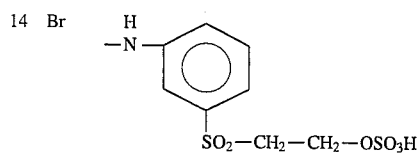 |
| Ex. | Q | T |
|---|---|---|
| 15 | Br | 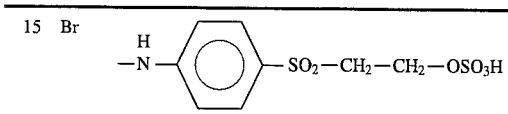 |
| 16 | Br | 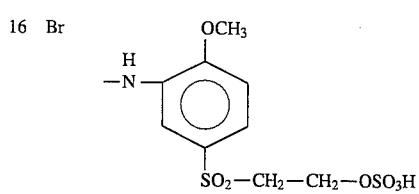 |
| 17 | Br | 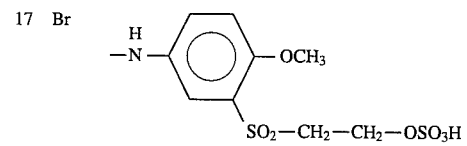 |
| 18 | Br | 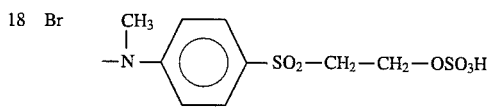 |
| 19 | Br | 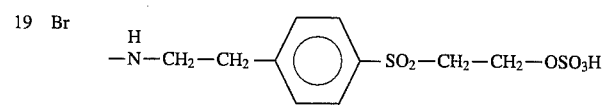 |
| 20 | Cl | 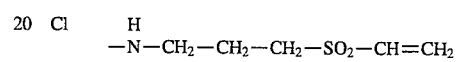 |
| 21 | Cl | 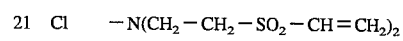 |
| 22 | Cl | 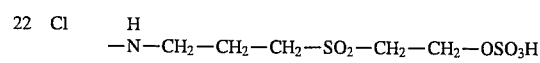 |
| 23 | Cl | 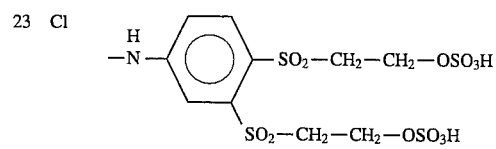 |
| 24 | Cl | 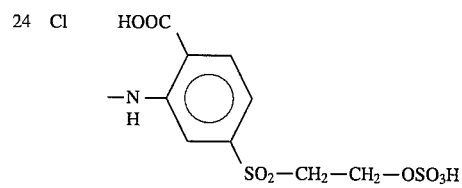 |
| 25 | Cl | 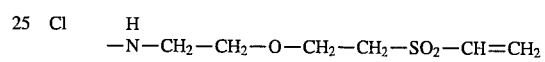 |
| 26 | Cl | 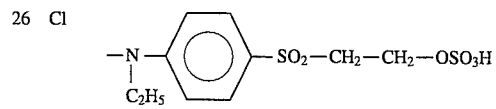 |

| | | |
|---|---|---|
| 27 | Br | 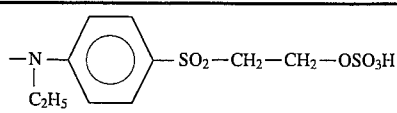 |
| 28 | Cl | 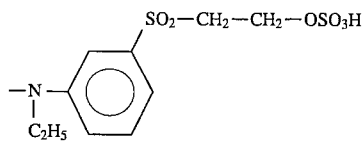 |
| 29 | Br | 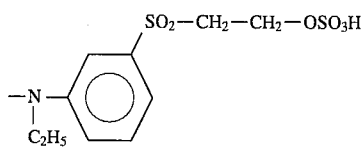 |
| 30 | Cl | $-N[CH_2-CH_2-CH_2-SO_2-CH_2-CH_2-Cl]_2$ |
| 31 | Cl | $-N[CH_2-CH_2-CH_2-SO_2-CH=CH_2]_2$ |

EXAMPLE 32

To 6.5 parts of 2,4,6-trichlorotriazine in 50 parts of water and 50 parts of ice, 1.5 parts of cyanamide in form of a 50% aqueous solution is added. The reaction mixture is stirred for 1.5 hours at 0°–3° C. at pH 8.5–9.5. After adjusting the pH to 7.0 of the resulting primary condensation product, a suspension of 10.1 parts 1-amino-4-[β-sulfatoethylsulfonyl]-benzene in 40 parts of water, which was adjusted to pH 4.5 using soda ash, is added. The mixture is stirred for 5 hours at 5°–8° C. while the pH is dropping to 1.5. The pH of the solution of the resulting secondary condensation product is adjusted to 5.5 with soda ash and clarified. This solution is then added over 4 hours to a solution of 13.7 parts of 2,9-diamino-6,13-dichlorotriphenodioxazine-1,8-disulfonic acid, which was brought to pH 5.0 using aqueous 5% LiOH. During the addition, the temperature is kept at 80°–85° C. and the pH at 3.0–3.5. The end of each condensation step can be monitored by using the high pedormance liquid chromatography. The resulting dyestuff solution is salted out with 15% by volume of sodium chloride. After drying and grinding it results in a blue dyestuff powder, which, if applied to cotton in one of the methods customary for reactive dyestuffs, produces brilliant strongly reddish bluish shades.

The dyestuff in form of the free acid has the following formula:

(λmax: 588 nm)

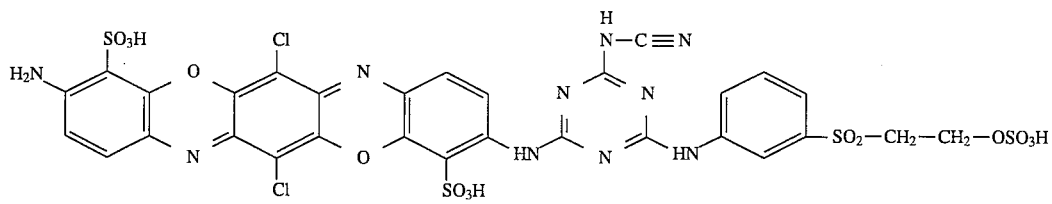

Further similar reddish blue dyestuffs can be obtained by replacing the 1,4-Diaminobenzene-3-sulfonic acid by 1,4-Diamino-benzene-3-carboxy acid during the chromophore synthesis, and using the procedure of the above samples. These compounds have the following general Formula B:

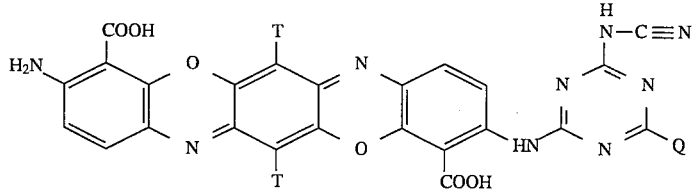

(Formula B)

Examples 33–44 illustrate compounds of the general Formula B wherein the substituents T and Q are as follows:

EXAMPLE 33–44

| Ex. | T | Q |
|---|---|---|
| 33 | Cl | ![structure] -N(H)-C6H4-SO2-CH2-CH2-OSO3H |

-continued

| Ex. | T | Q |
|---|---|---|
| 34 | Cl | −NH−C6H4−SO2−CH2−CH2−OSO3H |
| 35 | Cl | −NH−C6H3(CH3O)−SO2−CH2−CH2−OSO3H (CH3O ortho to NH) |
| 36 | Cl | −NH−C6H2(OCH3)2−SO2−CH2−CH2−OSO3H |
| 37 | Br | −NH−C6H4−SO2−CH2−CH2−OSO3H |
| 38 | Br | −NH−C6H4−SO2−CH2−CH2−OSO3H |
| 39 | Cl | −N(C2H5)−C6H4−SO2−CH2−CH2−OSO3H |
| 40 | Cl | −NH−C3H6−SO2−C2H4−OSO3H |
| 41 | Cl | −NH−C6H3(CH3)(OCH3)−SO2−C2H4−OSO3H |

-continued

| Ex. | T | Q |
|---|---|---|
| 42 | Cl | −NH−C6H3(COOH)−SO2−C2H4−OSO3H |
| 43 | Cl | Cl |
| 44 | Br | Cl |

EXAMPLE 45

21.8 parts of 2,9-diamino-6,13-dichlorotriphenodioxazine-1,8-disulfonic acid is suspended in 1000 parts of water and brought to pH 7.0 by using an aqueous solution of 5% LiOH. The reaction mixture is stirred for one hour until complete solution. The pH is adjusted with hydrochloric acid to 4.5 and 7.8 parts of 2,4,6-tdchlorotriazine is added. The reaction mixture is stirred for 3 hours at room temperature and the pH maintained at 4.5 using an aqueous solution of 5% LiOH. To the resulting pdmary condensation product 2.5 parts of cyanamide in form of a 50% aqueous solution is added and the pH adjusted to 9.0 using LiOH. The reaction mixture is heated up to 45°–40° C. by maintaining the pH. After stirring for 3 hours the reaction is completed. High performance liquid chromatography can be used in all steps to indicate the end of each condensation. The resulting dyestuff solution is spray dried. IT results in a blue powder, which, if applied to cotton in one of the methods customary for reactive dyestuffs, produces brilliant strongly reddish bluish shades.

The dyestuff in form of the free acid has the following formula:

(λmax: 582 nm)

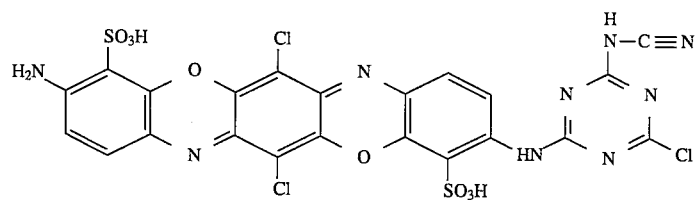

The above procedure can be used to produce other dyes having the following general Formula C:

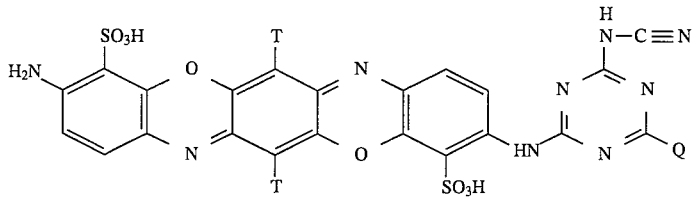

(Formula C)

The above procedure used to prepare a dye in the substituent Q and T are as follows:

EXAMPLE 46

| Ex. | T | Q |
|---|---|---|
| 46 | Cl | Cl |

Dyes prepared according to the present invention are suitable for the dyeing of cellulosic materials such as cotton, linen, viscose, rayon or staple fibers. They can be applied by any one of the usual dyeing and printing methods for reactive dyestuffs and yield on cellulosic materials, in the presence of alkaline agents, brilliant shades having excellent fastness properties, and high color yield and reduced cold water bleeding. These dyes may also be used on wool, silk or polyamide fibers.

The dyes of the present invention exhibit an unexpected and highly advantageous property in that they can be used at very low salt concentration in the dye bath while at the same time providing excellent dyeing yield. In the exhaust dyeing method using fiber reactive vinyl sulfone type dyes, one necessary auxiliary chemical is an electrolyte which is added to the dye bath to force the dye to migrate from solution to the fiber. The most commonly used electrolyte is an inorganic salt such as sodium sulfate or sodium chloride. In exhaust dyeing procedures, this electrolyte is generally employed in amounts from about 20–50 grams per liter to about 100 grams per liter of dye bath with the amount of electrolyte being proportionally higher as the amount of dye employed in the dyeing increases. A few fiber reactive dyes are known which can be used at reduced electrolyte concentration. However, some loss in dye yield occurs even with these dyes as the salt concentration is decreased in the dye bath. Surprisingly the dyes of this invention achieve optimum dye yield at a very low salt concentration. After the dyeing process is completed, the exhausted dye bath solution is discharged to waste water treatment facilities for removal of electrolyte and other residual dye bath chemicals.

The present invention provides a method for the exhaust dyeing of textiles using a select class of dyes at significantly lower levels of electrolyte in the dye bath with the attendant reduction in raw materials costs, reduced chemical discharge to the environment and reduced waste water treatment costs. An additional advantage is that the process of the invention unexpectedly gives a higher dyeing efficiency as evidenced by the achievement of higher dye build up values.

The advantages and unexpected properties of the dyes of this invention are shown in the following comparison of the invention with commercial pdor art dioxazine dyes.

Cotton test fabrics were dyed by the exhaust method at a 2% dye level and a liquid ratio of 10 to 1. The dyeing was conducted at 60° C. and in addition to the salt component, the dye bath contained 15% by weight soda ash and 1% by weight sodium hydroxide. The test specimens were dyed under substantially the same conditions and the color yield measured on a computer assisted spectrophotonomer with the color yield being measured in color density units (CDU).

| EXHAUST DYEING (Color Yield vs Soft Concentration) | | | | | |
|---|---|---|---|---|---|
| Example 1 (The Invention) | | | | | |
| Salt g/l | 100 | 50 | 30 | 20 | 10 |
| CDU | 1.067 | 1.044 | 1.127 | 1.094 | 1.11 |
| Rel. CDU % | 100 | 97.8 | 105.6 | 102.5 | 104.6 |
| C.I. Reactive Blue 198 (Prior Art) | | | | | |
| Salt g/l | 100 | 50 | 30 | 20 | 10 |
| CDU | 0.837 | 0.795 | 0.649 | 0.575 | 0.481 |
| Rel. CDU % | 100 | 90.7 | 77.5 | 68.7 | 57.5 |
| C.I. Reactive Blue 204 (Prior Art) | | | | | |
| Salt g/l | 100 | 50 | 30 | 20 | 10 |
| CDU | 1.638 | 1.486 | 1.376 | 1.319 | 1.06 |
| Rel. CDU % | 100 | 90.7 | 84 | 80.5 | 64.7 |

The invention may be embodied in other specific forms without departing from the spidt or essential characteristics thereof. Through this specification and the appended claims, a given chemical name or formula is intended to encompass all isomers of said name or formula where such isomers exist. The present embodiments are therefore to be considered in all respects as illustrative and not restrictive, the scope of the invention being indicated by the appended claims rather than by the foregoing description; and all changes which come within the meaning and equivalency of the claims are therefore intended to be embraced therein.

We claim:

1. A dyestuff of the formula:

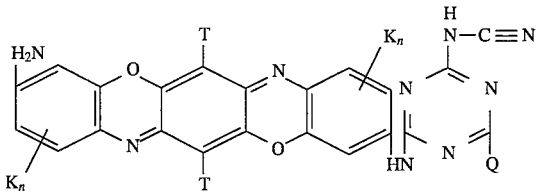

wherein T is independently selected from Cl and Br; Q is:

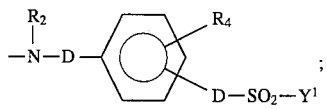

K is $SO_3H$;

n is independently selected from 0 or 1;

$R_2$ selected from hydrogen or $C_1$ to $C_4$ alkyl;

$R_4$ is selected from H, Cl, Br, $C_1$ to $C_4$ alkyl, or $C_1$ to $C_4$ alkoxy;

D is selected from a covalent bond or $C_1$ to $C_6$ alkylene which may be interrupted by a hetero atom selected from O, N or S; and $Y^1$ is selected from vinyl, β-sulfatoethyl, β-thiosulfatoethyl, β-halogenethyl or β-phosphatoethyl.
2. A dye according to claim 1 having the following formula:
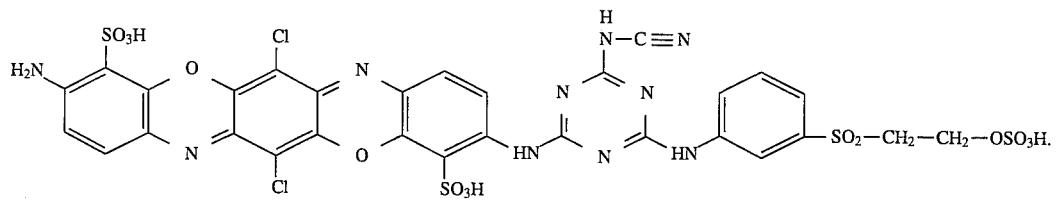
3. A dye according to claim 1 having the following formula:
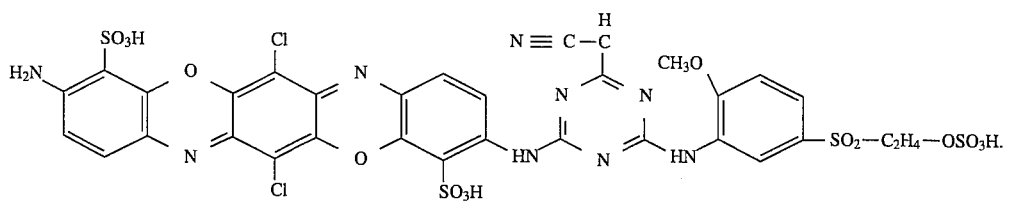
4. A dye according to claim 1 having the following formula:
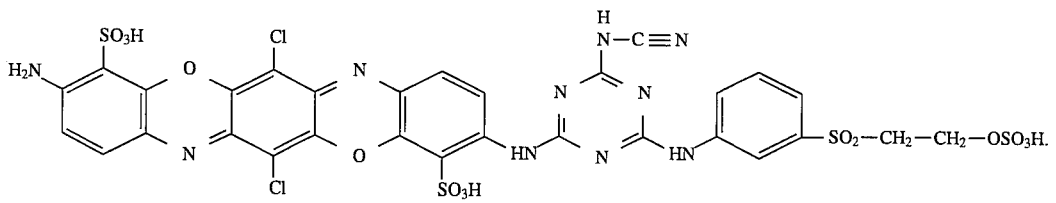
* * * * *